(12) United States Patent
Eastman et al.

(10) Patent No.: US 6,187,538 B1
(45) Date of Patent: *Feb. 13, 2001

(54) DIFFERENTIAL HYBRIDIZATION FOR RELATIVE QUANTIFICATION OF VARIANT POPULATIONS

(75) Inventors: P. Scott Eastman, Moraga; Michael S. Urdea, Alamo; Janice A. Kolberg, Hercules, all of CA (US)

(73) Assignee: Bayer Corporation, East Walpole, MA (US)

( * ) Notice: Under 35 U.S.C. 154(b), the term of this patent shall be extended for 0 days.

This patent is subject to a terminal disclaimer.

(21) Appl. No.: 09/075,501

(22) Filed: May 8, 1998

Related U.S. Application Data

(63) Continuation of application No. 08/688,088, filed on Jul. 29, 1996, now Pat. No. 5,827,648, which is a continuation of application No. 08/167,645, filed on Dec. 13, 1993, now abandoned.

(51) Int. Cl.⁷ .............................. C12Q 1/68; C12P 19/34; C12N 7/00; C07H 21/02; C07H 21/04
(52) U.S. Cl. ............................ 435/6; 435/91.1; 435/91.2; 435/235.1; 536/23.1; 536/24.3; 536/24.31; 536/24.32; 536/24.33
(58) Field of Search ............................ 435/6, 235.1, 91.1, 435/91.2; 536/23.1, 24.3, 24.31, 24.32, 24.33

(56) References Cited

U.S. PATENT DOCUMENTS 5,176,995 * 1/1993 Sninksy et al. ............................ 435/6
5,827,648 * 10/1998 Eastman et al. ............................ 435/6

OTHER PUBLICATIONS

Gingeras et al J. Inf. Dis. vol. 164 pp. 1066–1074, 1991.*

* cited by examiner

*Primary Examiner*—Kenneth R. Horlick
*Assistant Examiner*—Jeffrey Siew
(74) *Attorney, Agent, or Firm*—Dianne E. Reed; Reed & Associates

(57) ABSTRACT

This invention relates to a method of measuring the relative populations of first and second variants of a target nucleotide sequence of a target genome in a sample utilizing an amplification step, followed by probing with first and second variant probes and a control probe. Specific embodiments include an assay to monitor the conversion of codon 215 for HIV-1 reverse transcriptase from wild type to mutant form.

12 Claims, 1 Drawing Sheet

DIFFERENTIAL HYBRIDIZATION FOR RELATIVE QUANTIFICATION OF VARIANT POPULATIONS

CROSS-REFERENCE TO RELATED APPLICATIONS

This application is a continuation of U.S. patent application Ser. No. 08/688,088, filed Jul. 29, 1996, now issued as U.S. Pat. No. 5,827,648, which is a continuation of U.S. patent application Ser. No. 08/167,645, filed Dec. 13, 1993, abandoned.

FIELD OF THE INVENTION

This invention is in the field of nucleic acid diagnostics and the identification of single base or two base variation in target nucleotide sequences. More specifically, this invention relates to a method of using nucleic acid amplification and specific nucleic acid probes to determine the relative amounts of two variants of a nucleotide sequence in a target population.

BACKGROUND OF THE INVENTION

Various single base or two base point mutations in the human immunodeficiency virus (HIV) genome have been described which are associated with decreased susceptibility of HIV to drug therapy. Larder et al., *Science* (1989) 246:1155–1158; Kellam et al., *Proc. Natl. Acad. Sci.* (*USA*) (1992) 89:1934–1938. The identification of drug resistant strains has been associated with disease progression. One known example of this type of mutation is the two base mutation of amino acid 215 of the HIV-1 reverse transcriptase gene associated with zidovudine (AZT) resistance. Larder et al., supra.

Diagnosis of disease progression, as determined by onset of resistance mutations such as those described above, would be aided by the ability to determine the degree of conversion to the resistant mutant. Current methods, such as "selective PCR" are designed to detect presence or absence of the mutant sequence or wild type/mutant mixture, but are unable to accurately quantify amounts. Boucher et al., *Lancet* (1990) 336:585–590; Larder et al., *AIDS* (1991) 5:137–144.

A method for determining the presence or absence of allelic variants in a samples is described in Saiki et al., *Nature* (1986) 324:163–166; and Farr et al., *Proc. Natl. Acad. Sci.* (*USA*) (1987) 85:1629–1633. This method uses the polymerase chain reaction (PCR) technique to amplify a specific region of DNA. The amplified DNA is then used as a target for various radioactively-labelled oligonucleotide probes to identify point mutations and allelic sequence variation. This method has also been used to analyze the allelic genotype of a single sperm at the DNA level. Li et al., *Nature* (1988) 335:414–417.

An improved method is disclosed herein which provides a method for actually comparing the relative amounts of two variants (e.g., a wild type and a mutant) of a target nucleotide sequence of a target genome in a sample.

SUMMARY OF THE INVENTION

A method of measuring the relative populations of first and second variants of a target nucleotide sequence of a target genome in a sample is provided, the method comprising the steps of: (a) amplifying a region of the target genome containing the target nucleotide sequence and a control nucleotide sequence to obtain amplified target polynucleotides; (b) separating the amplified target polynucleotides into at least a first and second portion; (c) contacting the first portion of the amplified target polynucleotide with a first labelled polynucleotide probe complementary to the first variant of the target nucleotide sequence to obtain a first hybridized labelled polynucleotide probe, and contacting the second portion of the amplified target polynucleotide with a second labelled polynucleotide probe complementary to the second variant of the target nucleotide sequence to obtain a second hybridized labelled polynucleotide probe; (d) quantifying the amount of the first and second hybridized labelled polynucleotide probes; (e) contacting the first and second portions of the amplified target polynucleotide with a third labelled polynucleotide probe complementary to the control nucleotide sequence to obtain a third labelled polynucleotide probe; (f) quantifying the amount of the third hybridized labelled polynucleotide probe; (g) measuring the relative populations of the first and second variants by determining the relative amounts of the first and second hybridized labelled polynucleotide probes compared to the third hybridized labelled polynucleotide probe.

DETAILED DESCRIPTION OF THE INVENTION

Figure 1:
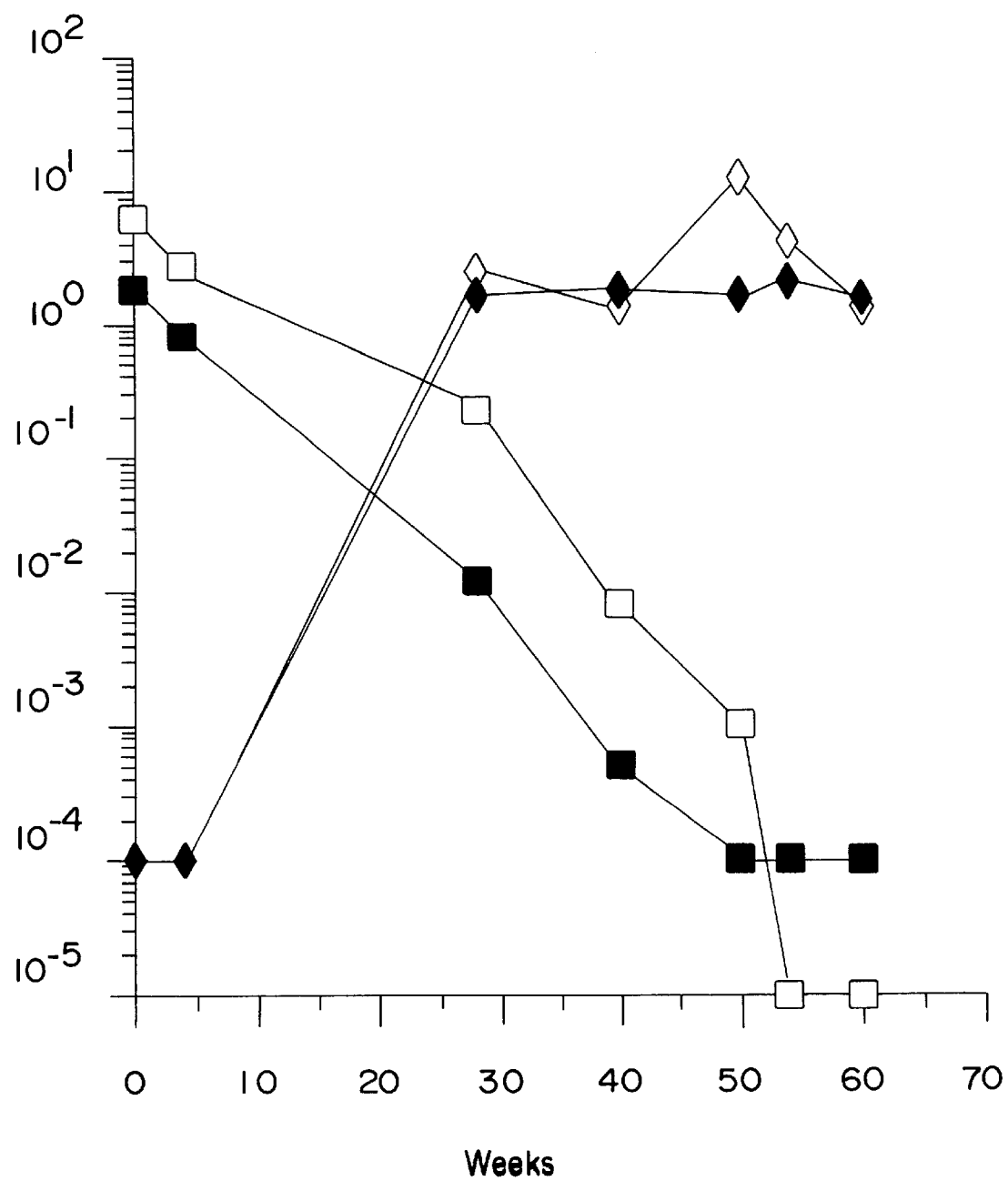
FIG. 1 monitors the conversion of amino acid 215 of HIV-1 reverse transcriptase from wild type to mutant as achieved by two embodiments of the assay of the current invention.

The invention described herein draws on previously published work and pending patent applications. By way of example, such work consists of scientific papers, patents or pending patent applications. All of these publications and applications, cited previously or below are hereby incorporated by reference.

Definitions

By "PCR" is meant herein the polymerase chain reaction (PCR) technique, disclosed by Mullis in U.S. Pat. Nos. 4,683,195 (Mullis et al) and 4,683,202, incorporated herein by reference. In the PCR technique, short oligonucleotide primers are prepared which match opposite ends of a desired sequence. The sequence between the primers need not be known. A sample of DNA (or RNA) is extracted and denatured (preferably by heat). Then, oligonucleotide primers are added in molar excess, along with dNTPs and a polymerase (preferably Taq polymerase, which is stable to heat). The DNA is replicated, then again denatured. This results in two "long products," which begin with the respective primers, and the two original strands (per duplex DNA molecule). The reaction mixture is then returned to polymerizing conditions (e.g., by lowering the temperature, inactivating a denaturing agent, or adding more polymerase), and a second cycle initiated. The second cycle provides the two original strands, the two long products from cycle 1, two new long products (replicated from the original strands), and two "short products" replicated from the long products. The short products have the sequence of the target sequence (sense or antisense) with a primer at each end. On each additional cycle, an additional two long products are produced, and a number of short products equal to the number of long and short products remaining at the end of the previous cycle. Thus, the number of short products grows exponentially with each cycle. This amplification of a specific analyte sequence allows the detection of extremely small quantities of DNA.

The term "3SR" as used herein refers to a method of target nucleic acid amplification also known as the "self-sustained sequence replication" system as described in European Patent Publication No. 373,960 (published Jun. 20, 1990).

The term "LCR" as used herein refers to a method of target nucleic acid amplification also known as the "ligase chain reaction" as described by Barany, *Proc. Nati. Acad. Sci. (USA)* (1991) 88:189–193.

The term "polynucleotide" as used herein refers to a polymeric form of nucleotides of any length, either ribonucleotides or deoxyribonucleotides. This term refers only to the primary structure of the molecule. Thus, this term includes double- and single-stranded DNA and RNA. It also includes known types of modifications, for example, labels which are known in the art, methylation, "caps", substitution of one or more of the naturally occurring nucleotides with an analog, internucleotide modifications such as, for example, those with uncharged linkages (e.g., methyl phosphonates, phosphotriesters, phosphoramidates, carbamates, etc.) and with charged linkages (e.g., phosphorothioates, phosphorodithioates, etc.), those containing pendant moieties, such as, for example proteins (including for e.g., nucleases, toxins, antibodies, signal peptides, poly-L-lysine, etc.), those with intercalators (e.g., acridine, psoralen, etc.), those containing chelators (e.g., metals, radioactive metals, boron, oxidative metals, etc.), those containing alkylators, those with modified linkages (e.g., alpha anomeric nucleic acids, etc.), peptide nucleic acids ("PNAs"), as well as unmodified forms of the polynucleotide.

The term "target genome" as used herein refers to a polynucleotide encoding one or more proteins sought to be analyzed by the method of this invention. The target genome can be viral or bacterial, but is preferably a viral genome carried by a mammalian individual, and may be DNA or RNA. Target genomes of this invention include, but are not limited to, hepatitis A virus (HAV), hepatitis B virus (HBV), hepatitis C virus (HCV), hepatitis D virus (HDV), human immunodeficiency virus (HIV), human papilloma virus (HPV), cytomegalovirus (CMV), herpes simplex virus (HSV) and bovine papilloma virus (BPV).

By "target nucleotide sequence" is meant a sequence contained in the target genome which is known or believed to be capable of changing from a wild type sequence to a mutant sequence. One example of a target nucleotide sequence is a nucleotide sequence corresponding to a portion of the HIV-1 genome which includes the nucleotide sequence encoding amino acid 215 of the HIV-1 reverse transcriptase gene.

By "control nucleotide sequence" is meant a sequence contained in the target genome which is known or believed to be relatively stable, or unlikely to be capable of changing from a wild type sequence to a mutant sequence.

As used herein, the term "probe" refers to a structure comprised of a polynucleotide, as defined above, which contains a nucleic acid sequence complementary to a nucleic acid sequence present in the target molecule. The polynucleotide regions of probes may be composed of DNA, and/or RNA, and/or synthetic nucleotide analogs.

It will be appreciated that the binding sequences need not have perfect complementarity to provide stable hybrids. In many situations, stable hybrids will form where fewer than about 10% of the bases are mismatches, ignoring loops of four or more nucleotides. However, the high sensitivity of this assay will usually require that the probes that hybridize to the first and second variants of the target nucleotide sequence and the control nucleotide sequence have 100% homology to their targets. Accordingly, as used herein the term "complementary" intends to refer to an oligonucleotide that forms a stable duplex with its "complement" under assay conditions, generally where there is about 100% homology, while the term "substantially complementary" intends to refer to an oligonucleotide that forms a stable duplex with its "complement" under assay conditions, generally where there is about 90% or greater homology.

As used herein, the term "sample" refers to a fluid or tissue of a mammalian individual (e.g., an anthropoid or human) that commonly contains the target genome sought to be characterized. Such components are known in the art and include, without limitation, blood, plasma, serum, spinal fluid, lymph fluid, secretions of the respiratory, intestinal or genitourinary tracts, tears, saliva, milk, and white blood cells.

The Method

Although any similar or equivalent methods and materials may be employed in the practice or testing of the present invention, the preferred methods and materials are now described.

The method of this invention is a method for measuring the relative populations of first and second variants of a target nucleotide sequence of a target genome in a sample. In the first step of this method samples containing the target genome are obtained from an individual and prepared for analysis. Methods of sample preparation for nucleic acid assays are well-known in the art.

The desired region of the target genome is then amplified. Methods of target nucleic acid amplification are known in the art, and include PCR, 3SR and LCR. In preferred embodiments of this invention, the region is amplified using PCR as described herein. Suitable PCR primers are prepared by means known to those of ordinary skill in the art, for example by cloning and restriction of appropriate sequences, or by direct chemical synthesis. For example, one may employ the phosphotriester method described by S. A. Narang et al, *Meth Enzymol* (1979) 68:90, and U.S. Pat. No. 4,356,270, incorporated herein by reference. Alternatively, one may use the phosphodiester method disclosed in E. L. Brown et al, *Meth Enzymol* (1979) 68:109, incorporated herein by reference. Other methods include the phosphoramidite method disclosed in Beaucage et al, *Tetrahedron Lett* (1981) 22:1859–62, and the solid support method in U.S. Pat. No. 4,458,066. The primers may also be labeled, if desired, by incorporating means detectable by spectroscopic, photochemical, biochemical, immunochemical, or chemical means. For example, the primer may include $^{32}p$, fluorescent. dyes, electron-dense reagents, enzymes (as commonly used in ELISAs), biotin, or haptens or proteins for which antisera or monoclonal antibodies are available. The label should be selected to withstand denaturing conditions if it is to be attached directly to the primer.

When the analyte strand has been separated from contaminating material, and has been displaced from the solid support (if desired), it is ready to be used as a template for the synthesis of additional nucleic acid strands. This synthesis can be performed using any suitable method. The reaction is generally conducted in a buffered aqueous solution, preferably at a pH of 7–9, most preferably about 8. Preferably, a molar excess (for cloned nucleic acid, usually about 1000:1 primer/template, and for genomic or viral nucleic acid, usually about $10^8:1$ primer template) of the two oligonucleotide primers is added to the buffer containing the separated template strands. It is understood, however, that the amount of complementary strand may not be known, so the amount of primer relative to the amount of complementary strand cannot be determined with certainty. A large molar excess is preferred to improve the efficiency of the process.

The deoxyribonucleoside triphosphates dATP, dCTP, dGTP and dTTP are also added to the synthesis mixture in adequate amounts and the resulting solution is heated to about 90–100° C. for about 1 to 10 minutes, preferably from 1 to 4 minutes. After heating, the solution is allowed to cool to room temperature, which is preferred for the primer hybridization. To the cooled mixture is added a polymerization agent, and the reaction is conducted under conditions known in the art. This synthesis reaction may occur at from room temperature up to a temperature above which the polymerization agent no longer functions efficiently. Thus, for example, if an *E. coli* DNA polymerase is used as the polymerizing agent, the maximum temperature is generally no greater than about 40° C. Most conveniently, the reaction using *E. coli* polymerase occurs at room temperature. Where greater stringency is desired, the reaction is performed using the thermostable enzyme Taq polymerase at elevated temperature.

The polymerization agent may be any compound or system which will function to accomplish the synthesis of primer extension products from nucleotide triphosphates, including enzymes. Suitable enzymes for this purpose include, for example, *E. coli* DNA polymerase I, Klenow fragment of *E. coli* DNA polymerase I, T4 DNA polymerase, other available DNA polymerases, reverse transcriptase, and other enzymes, including heat-stable enzymes such as Taq polymerase, which will facilitate combination of the nucleotides in the proper manner to form the primer extension products which are complementary to each nucleic acid strand. Generally, the synthesis will be initiated at the 3' end of each primer and proceed in the 5' direction along the template strand, until synthesis terminates, producing molecules of different lengths. There may be agents, however, which initiate synthesis at the 5' end and proceed in the other direction, using the same process as described above: use of such agents in the process of the invention is also to be considered within the scope of this invention.

The newly synthesized analyte-complementary strand and the original analyte nucleic acid strand form a double-stranded molecule which is used in the succeeding steps of the process. In the next step, the strands of the duplex molecule are separated using any of the procedures described above to provide single-stranded molecules.

New nucleic acid is synthesized on the single-stranded molecules. Additional polymerization agent, nucleotides and primers may be added if necessary for the reaction to proceed under the conditions prescribed above. Again, the synthesis will be initiated at one end of the oligonucleotide primers and will proceed along the single strands of the template to produce additional nucleic acid. After this step, half of the extension product will consist of the specific nucleic acid sequence bounded by the two primers.

The steps of strand separation and extension product synthesis can be repeated as often as needed to produce the desired quantity of the specific nucleic acid sequence. As will be described in further detail below, the amount of the specific nucleic acid sequence produced will accumulate in an exponential fashion.

If desired, one may amplify the target sequence in two stages, using nested primers. This variation may be used as a means for increasing the specificity of the reaction. The first phase of PCR may be performed with "normal" primers, i.e., primers which do not arrest polymerization, while the second phase is performed with the arresting primers of the invention. The primer binding regions are selected so that the second set (arresting primers) bind to regions of the analyte sequence between the primer binding regions for the first set (thus insuring that the second set binding regions will be amplified if present). The amplification process may be terminated at any time once a detectable quantity of polynucleotide has accumulated.

The amplified target polynucleotide is then apportioned into at least two portions. The hybridization assay can be performed in solution or with a solid support. Solution phase hybridization procedures are well-known in the art, e.g., the hybridization protection (HPA) chemiluminescent assay marketed by GenProbe (San Diego, Calif.) utilizing acridinium ester labelled probes. If a solution-phase assay is employed, apportioning may be accomplished by binding to a solid support. The amplified target may be bound directly to a conventional support such as nitrocellulose filters or nylon membranes. In an alternative embodiment, the amplified target polynucleotide could be modified during amplification to include a nucleotide modified with a ligand or receptor capable of binding to a support-bound receptor or ligand. For example, the last round of amplification can include biotinylated thymidine, or PCR can be performed using biotinylated primers, and the target would be contacted with an avidinylated support. Other receptors include thyroxine binding globulins, lectins, enzymes, antibodies and the like, while ligands include thyroxine, carbohydrates, enzyme substrates, antigens and the like. Other receptor-ligand pairs are known in the art. In still another embodiment, the amplified target polynucleotide can be captured in a sandwich assay as described in U.S. Pat. No. 4,868,105 to Urdea et al., the disclosure of which is incorporated herein by reference.

Once the amplified target is apportioned, it is then labelled with the appropriate first, second and control probes complementary to the first variant, second variant and control nucleotide sequences in the amplified target. In general, suitable detection means are employed to determine the presence and/or quantity of target sequence present in the amplified reaction mixture. Presence of the target sequence in the sample is generally determined by the presence or absence of binding by a labeled probe.

The labelled probe, in addition to including the complementary sequence discussed above, also includes one or more molecules which directly or indirectly provide for a detectable signal. The labels may be bound to individual members of the complementary sequence, or may be present as a terminal member or terminal tail having a plurality of labels. Various means for providing labels bound to the sequence have been reported, e.g., Leary et al., *Proc. Natl. Acad. Sci. (USA)* (1983) 80:4045; Renz and Kurz, *Nucl. Acid Res.* (1984) 12:3435; Richardson and Gumport, *Nucl. Acid Res.* (1983) 11:6167; Smith et al., *Nucl. Acid Res.* (1985) 13:2399; and Meinkoth and Wahl, *Anal, Biochem.* (1984) 138:267. The labels may be bound either covalently or non-covalently to the complementary sequence.

Labels which may be employed include radionuclides, fluorescers, chemiluminescers, dyes, enzymes, enzyme substrates, enzyme cofactors, enzyme inhibitors, enzyme subunits, metal ions, and the like. Specific labels include fluorescein, rhodamine, Texas red, phycoerythrin, umbelliferone, luminol, NADPH, beta-galactosidase, horseradish peroxidase, alkaline phosphatase, etc. By providing a terminal group on the complementary sequence with a convenient functionality, various labels may be joined by known methods. Thus, one can provide for a carboxy, thiol, amine, hydrazine or other functionality to which the various labels may be joined without detrimentally affecting duplex formation.

Depending upon the nature of the label, various techniques can be employed for detecting and quantifying the presence of the label. For fluorescers, a large number of different fluorometers are available. For chemiluminescers, luminometers or films are available. With enzymes, a fluorescent, chemiluminescent, or colored product can be provided and determined fluorometrically, luminometrically, spectro-photometrically or visually. The various labels which have been employed in immunoassays and the techniques applicable to immunoassays can be employed with the subject assays.

A first portion of the amplified target is probed with the first variant probe, while a second portion is probed with the second variant probe. Both portions are also probed with a control probe. It will be apparent to one skilled in the art that the two probing steps may be performed in any order, as long as the first round of probe is appropriately detached and washed from the target before the second round is added. Alternatively, the control probe assay may be accomplished by initially dividing the amplified target into three substantially equivalent portions and probing these portions with the first variant, second variant and control probes, respectively.

After all the probing steps are completed, the amount of first variant and second variant sequences relative to the generic probe is determined. These values are then normalized to 100% mutant and 100% wild type controls. An example of a method of calculating relative populations where the first variant is a wild type sequence and the second variant is a mutant sequence is as follows: The assay is performed on test samples as well as a known wild type ("WTCon") and a known mutant ("MutCon") sample. Let:

$WT_{test}$=amount of wild type probe bound to test sample
$MUT_{test}$=amount of mutant probe bound to test sample
$CON_{test}$=amount of control probe bound to test sample
$WT_{WTCon}$=amount of wild type probe bound to WTCon
$CON_{WTCon}$=amount of control probe bound to WTCon
$MUT_{MutCon}$=amount of mutant probe bound to MutCon
$CON_{MutCon}$=amount of control probe bound to MutCon.

The percentage of wild type in the sample is then $X_{test}=WT_{test}/CON_{test}$. If $X_{WTCon}=WT_{WTCon}/CON_{WTCon}$, then the normalized percentage of wild type in the sample is $X_{testNorm}=X_{test}/X_{WTCon}$. Similarly, the percentage of mutant in the sample is $Y_{test}=MUT_{test}/CON_{test}$. If $Y_{MuTCon}=MUT_{MutCon}/CON_{MutCon}$, then the normalized percentage of mutant in the sample is $Y_{testNorm}=Y_{test}/Y_{MutCon}$. Finally, the ratio of mutant to wild type in the sample is calculated as $Y_{testNorm}/X_{testNorm}$.

Kits for carrying out the comparison amplified nucleic acid hybridization assays according to the invention will comprise in packaged combination at least the following reagents: first, second and third labelled probes corresponding to first variant, second variant and control nucleotide sequences, first and second supports capable of binding the amplified target, first and second primers specific for amplification of the target region. The kit may also include a DNA polymerase such as E. coli DNA Polymerase I (Klenow fragment), Taq polymerase or the like, a de-naturation reagent for denaturing the analyte, hybridization buffers, wash solutions, enzyme substrates, negative and positive controls and written instructions for carrying out the assay.

The present invention will now be illustrated by reference to the following examples which set forth particularly advantageous embodiments. However, it should be noted that these embodiments are illustrative and are not to be construed as restricting the invention in any way.

EXAMPLE 1

Radiolabelled Relative Quantification Assay of the Mutation of Codon 215 in HIV-1 Reverse Transcriptase A. Sample Preparation 1 ml of each sample was removed to a new tube and spun for 10 minutes on high in an Eppendorf microfuge to pellet any cell debris. 900 μl of the supernatant was transferred to a new tube and spun at 23,500×g at 4° C. for 1 hour. 800 μl of the supernatant was carefully removed without disturbing the pellet and discarded.

300 μl of Lysis Reagent (157 mM HEPES pH 7.5, 12.5 mM EDTA pH8.0, 1.6% lithium lauryl sulfate, 19 μg/ml salmon sperm DNA, 627.5 mM LiCl, 1 mg/ml proteinase K, 0.05% $NaN_3$, and 0.05% Proclin-300 in DEPC-treated $H_2O$) was transferred to the remaining 100 μl and pellet in each sample tube. The samples were vortexed well and incubated at 63° C. for two hours. 400 μl phenol was added to each tube with vortexing, followed by 400 μl chloroformisoamyl alcohol (24:1, v/v) and more vortexing. The tubes were spun on high in an Eppendorf microfuge for 5 minutes to separate the phases. The aqueous layer was removed to a fresh tube containing 400 μl phenol and the phenolchloroform extraction and centrifugation steps were repeated. The aqueous layer was removed to a fresh tube containing 400 μl chloroformisoamyl alcohol (24:1, v/v) and vortexed. The aqueous layer was removed to a fresh tube containing 40 μl of 3M sodium acetate and vortexed. 1 ml of 100% ethanol was transferred, and the tubes were vortexed and stored at −80° C. overnight.

All samples were then centrifuged in an Eppendorf microfuge on high for 20 minutes. All but about 100 μl of the supernatant was removed and 1 ml of 70% ethanol was transferred to each tube and centrifugation repeated. The supernatant was removed and excess ethanol permitted to evaporate. 90 μl of DEPC (diethyl pyrocarbonate)-treated water was added to each tube and vortexed. Aliquots were removed for PCR and samples stored at −80° C.

B. PCR Amplification

RT PCR of the HIV-1 RT Gene was performed as a modification of the procedure described by Richman et al., J. Infect. Dis. (1991) 164:1075–1081. cDNA synthesis was performed on 100 μl plasma equivalents in 100 μl buffer containing 50 mM Tris pH 8.3, 2.5 mM $MgCl_2$, 10 mM KCl, 0.1 mg/ml bovine serum albumin (BSA), 0.25 mM each of the four deoxynucleoside triphosphates, and 0.25 μg 5RT primer (SEQ. ID NO:1) and 3RT primer (SEQ. ID NO:2). Samples were heated to 65° C. for 90 seconds, then cooled to 42° C. for 1 minute followed by the addition of 200 units of Moloney murine leukemia virus reverse transcriptase (GIBCO/BRL) and incubation at 42° C. for 15 minutes. The samples were heated to 100° C. for 2 minutes, then cooled to 55° C. for 5 minutes during which time 2.5 U Taq polymerase (Perkin Elmer) was added. The temperature was raised to 72° C. for 3 minutes followed by 40 cycles of denaturation at 94° C. for 1 minute, annealing at 55° C. for 1 minute and extension at 72° C. for 3 minutes.

C. Radiolabelled Analysis of PCR Product

Ten microliters of PCR product (10 μl plasma equivalents) was blotted onto duplicate GeneScreen Plus (NEN Dupont) nylon membranes using the manufacturer's recommended procedures. One membrane was hybridized as described by Richman et al. with 10 picomoles (pmol) $^{32}$P-kinased probe specific for the wild-type (WT) sequence at codon 215 having the sequence (SEQ. ID NO:1). The other membrane was hybridized in the same manner with 10 pmol $^{32}$P-kinased probe specific for the mutant sequence having the sequence (SEQ. ID NO:2). The blots were allowed to hybridize overnight at 50° C. followed by 5 washes in 1×SSPE, 1% SDS at 50° C. for 5 minutes. Autoradiography was performed at −80° C. with one intensifying screen. The amount of radioactivity bound to each spot was determined with an AMBIS 4000 Image Analyzer. Both blots were stripped according to the manufacturer's recommended procedure and subsequently hybridized with 10 pmol kinased probe to a conserved region of the RT gene ("HIV generic probe" or "GNR") having the sequence (SEQ. ID NO:3) as described above. The blots were then washed and autoradiography and image analysis performed as described above.

Table 1 shows the results of using this assay to monitor the wild-type to mutant ratio in a patient being treated with zidovudine (AZT) as well as acyclovir (Acy) and dideoxyinosine (ddI) over a period of 202 days. Total viral load was also monitored (HV eq/ml).

EXAMPLE 2

Non-Radiolabelled Relative Quantification Assay of the Mutation of Codon 215 in HIV-1 Reverse Transcriptase Sample preparation and PCR Amplification were performed as in Example 1A–B above. The wild type, mutant and HIV generic probes were as in Example 1C with the following modification: Instead of adding a $^{32}$P label, each oligonucleotide probe includes an additional $N^4$-(6-amino caproyl-2-aminoethyl)cytosine residue at the 3' end. An alkaline phosphatase molecule is then coupled through the free amino group using the bifunctional linking agent 1,4-diisothiocyanatobenzene (DITC).

Hybridization wells were allowed to warm to room temperature. 400 μl of 200 mM Tris pH 7.5, 0.1×SSC, 0.1% SDS was added to each well and incubated at room temperature for 10 minutes. The wells were aspirated and the previous step repeated. The wells were rinsed one final time with 50 mM $Na^+PO_4^-$buffer, pH~5.5. (3.95 mls 1 M $Na_2HPO_4$+46.05 mls 1 M $NaH_2PO_4$, QS to 500 mls with $H_2O$). 1 μl of PCR product (WT and Mut) was diluted into 49 μl of 50 mM $Na^+PO_4^-$buffer, pH~5.5 and vortexed well. The Mut and WT PCR products were then added to the appropriate wells and incubated at room temperature for 30 minutes.

All wells were aspirated and washed three times with 400 μl 200 mM Tris pH 7.5, 01×SSC, 0.1% SDS. 400 μl 0.15 N NaOH was added to each well. The wells were then aspirated and 400 μl 0.15 N NaOH added to each, followed by incubation at room temperature for 5 minutes. Each well was aspirated and washed three times with 400 μl 200 mM Tris pH 7.5, 0.1×SSC, 0.1% SDS. Then 100 μl hybridization solution (5×SSC, 1% SDS, 0.5% polyvinyl pyrrolidone, 0.5% BSA) containing 1 pmol of the appropriate probe (wild type or mutant, as in Example 1C) was added to each well as appropriate and incubated for 1 hour at 50° C. Each well was rinsed with 400 μl 0.9×SSC, 0.1% SDS prewarmed to 50° C., washed twice with 400 μl 0.9×SSC, 0.1% SDS for 5 minutes at 50° C., washed twice with 400 μl 0.9×SSC, 0.1% Triton X-100 for 5 minutes at 50° C., and then washed three times with 400 μl 0.9×SSC for 5 minutes at room temperature, 200 μl p-nitrophenyl phosphate substrate solution was then added to each well and incubated at 37° C. for 30 minutes. The absorbance was measured at 405 nM using a microplate reader.

The steps in the previous paragraph were repeated, this time hybridizing with the RT generic probe (as in Example 1) at 50° C. and washing at 50° C. Table 2 shows the results of using this assay to monitor three patients (patient 1=samples 15–20, patient 2=samples 21–24, patient 3=samples 35–41) undergoing AZT therapy.

EXAMPLE 3

Comparison of Radioisotope and Non-Radioisotope Assays

The radioactive and non-radioactive assays of Examples 1 and 2 were compared. Samples from a patient over time were analyzed by both methods to obtain mutant:wild type ratios. Total viral load was also measured. Percentage of wild type and mutant in each sample was calculated over time, and the results are shown in FIG. 1. Squares represent wild type and diamonds represent mutant; open figures represent the radioisotope asssay, filled figures represent the non-radioisotone assay.

TABLE 1

CLINICAL INFORMATION AND HYBRIDIZATION DATA FOR PATIENT NO. 8

| Days | HIV equ/mL | CD4 | Antiviral* | WT | Raw Counts GNR(WT) | GNR | WT: Control | Mutant | Raw Counts GNR(Mut) | Mut: GNR | Mut: Control | Mut: WT |
|---|---|---|---|---|---|---|---|---|---|---|---|---|
| −63 | | 280 | AZT/Acy | | | | | | | | | |
| −49 | 37,000 | | AZT/Acy | 2,554 | 44,647 | 0.06 | 0.11 | 2,558 | 6,348 | 0.40 | 0.09 | 0.79 |
| −42 | 42,000 | | AZT | 7,897 | 47,112 | 0.17 | 0.32 | 15,364 | 21,401 | 0.72 | 0.16 | 0.48 |
| 1 | 22,000 | | AZT/ddI | 2,543 | 27,017 | 0.09 | 0.18 | 3,255 | 3,443 | 0.95 | 0.20 | 1.13 |
| 7 | 9,000 | | AZT/ddI | 2,476 | 25,450 | 0.10 | 0.19 | 8,710 | 13,963 | 0.62 | 0.13 | 0.72 |
| 14 | | 708 | AZT/ddI | | | | | | | | | |

TABLE 1-continued

CLINICAL INFORMATION AND HYBRIDIZATION DATA FOR PATIENT NO. 8

| Days | HIV equ/mL | CD4 | Antiviral* | Raw Counts WT | GNR(WT) | WT: GNR | WT: Control | Raw Counts Mutant | GNR(Mut) | Mut: GNR | Mut: Control | Mut: WT |
|---|---|---|---|---|---|---|---|---|---|---|---|---|
| 18 | 5,000 | 490 | AZT/ddI | 1,735 | 27,125 | 0.06 | 0.12 | 9,846 | 19,372 | 0.51 | 0.11 | 0.89 |
| 62 | 11,000 | | AZT/ddI | 10,313 | 8,411 | 1.23 | 2.36 | 3,616 | 4,826 | 0.75 | 0.16 | 0.07 |
| 139 | 54,000 | 497 | AZT/ddI | 12,550 | 40,926 | 0.31 | 0.59 | 10,587 | 34,711 | 0.31 | 0.07 | 0.11 |
| — | | | Mix-M | 18,879 | 102,205 | 0.18 | 0.36 | 47,399 | 31,351 | 1.51 | 0.33 | 0.92 |
| — | | | Mutant | 0 | 87,536 | 0.00 | 0.00 | 135,707 | 29,306 | 4.63 | 1.00 | |
| — | | | WT | 188,852 | 363,510 | 0.52 | 1.00 | 0 | 37,543 | 0.00 | 0.00 | |

*Acy = Acyclovir
The amounts of WT and mutant PCR product were determined by normalization to the WT and mutant controls.

TABLE 2

| Sample No. | Mut | GNR | Mut:GNR | Normalized Mut:GNR | WT | GNR | WT:GNR | Normalized WT:GNR | Mut:WT |
|---|---|---|---|---|---|---|---|---|---|
| 15 | 0.201 | 0.777 | 0.259 | 0.810 | 0.224 | 0.804 | 0.279 | 0.193 | 4.2 |
| 16 | 1.16 | 2.764 | 0.420 | 1.314 | 0.669 | 2.953 | 0.237 | 1.164 | 8.0 |
| 17 | 0.012 | 0.022 | 0.545 | 1.708 | 0.001 | 0.022 | 0.045 | 0.032 | 54.1 |
| 18 | 0.422 | 0.952 | 0.443 | 1.388 | 0.001 | 1.014 | 0.001 | 0.001 | 2,027 |
| 19 | 0.248 | 0.618 | 0.401 | 1.256 | 0.001 | 0.593 | 0.002 | 0.001 | 1,073 |
| 20 | 0.822 | 1.613 | 0.510 | 1.596 | 0.003 | 1.824 | 0.002 | 0.001 | 1,397 |
| 21 | 0.549 | 1.666 | 0.330 | 1.032 | 0.002 | 1.392 | 0.001 | 0.001 | 1,034 |
| 22 | 1.086 | 2.581 | 0.421 | 1.317 | 0.011 | 2.506 | 0.004 | 0.003 | 432 |
| 23 | 0.218 | 0.617 | 0.353 | 1.106 | 0.001 | 0.485 | 0.002 | 0.001 | 773 |
| 24 | 0.776 | 1.994 | 0.389 | 1.218 | 0.005 | 2.106 | 0.002 | 0.002 | 739 |
| 35 | 0 | 0.06 | 0.000 | 0.000 | 0.042 | 0.016 | 2.625 | 1.823 | 0.000 |
| 36 | 0 | 0.035 | 0.000 | 0.000 | 0.066 | 0.056 | 1.179 | 0.818 | 0.000 |
| 37 | 0.121 | 0.233 | 0.519 | 1.626 | 0.005 | 0.28 | 0.018 | 0.012 | 131 |
| 38 | 0.067 | 0.123 | 0.545 | 1.705 | 0.001 | 0.153 | 0.007 | 0.005 | 376 |
| 39 | 0.376 | 0.753 | 0.499 | 1.563 | 0.001 | 0.67 | 0.001 | 0.001 | 1,508 |
| 40 | 0.371 | 0.601 | 0.617 | 1.933 | 0.001 | 0.696 | 0.001 | 0.001 | 1,937 |
| 41 | 0.269 | 0.557 | 0.483 | 1.512 | 0.001 | 0.574 | 0.002 | 0.001 | 1,250 |
| Mut | 1.238 | 3.876 | 0.319 | 1.000 | 0.011 | 3.8 | 0.003 | 0.002 | 497 |
| Mix | 0.775 | 1.911 | 0.406 | 1.270 | 0.188 | 2.203 | 0.085 | 0.059 | 21 |
| WT | 0.105 | 2.033 | 0.052 | 0.162 | 3.871 | 2.688 | 1.440 | 1.000 | 0.162 |

We claim:

1. A method of measuring the relative populations of first and second variants of a target nucleotide sequence of a target genome in a sample, the method comprising the steps of:
   (a) amplifying a region of the target genome containing both the target nucleotide sequence and a control nucleotide sequence to obtain amplified target polynucleotides;
   (b) separating the amplified target polynucleotides into at least a first and second portion;
   (c) contacting the first portion of the amplified target polynucleotide with a first labelled polynucleotide probe complementary to the first variant of the target nucleotide sequence to obtain a first hybridized labelled polynucleotide probe, and contacting the second portion of the amplified target polynucleotide with a second labelled polynucleotide probe complementary to the second variant of the target nucleotide sequence to obtain a second hybridized labelled polynucleotide probe;
   (d) quantifying the amount of the first and second hybridized labelled polynucleotide probes;
   (e) contacting the amplified target polynucleotide with a third labelled polynucleotide probe complementary to the control nucleotide sequence contained in the target genome to obtain a third labelled polynucleotide probe;
   (f) quantifying the amount of the third hybridized labelled polynucleotide probe;
   (g) measuring the relative populations of the first and second variants by determining the relative amounts of the first and second hybridized labelled polynucleotide probes compared to the third hybridized labelled polynucleotide probe.

2. The method of claim 1 wherein the first and second variants of the target nucleotide sequence are wild type and mutant nucleotide sequences, respectively.

3. The method of claim 2 wherein the target genome is the human immunodeficiency virus (HIV) genome.

4. The method of claim 3 wherein the wild type and mutant nucleotide sequences comprise the nucleotides encoding amino acid 215 of the HIV-1 reverse transcriptase gene.

5. The method of claim 4 wherein the control nucleotide sequence contained in the target genome comprises nucleotides encoding amino acids 151 through 157.

6. The method of claim 1 wherein in step (b), the first and second portions of the amplified target nucleotides are prepared by binding the amplified target nucleotides to a first and second solid support.

7. The method of claim 1 wherein said labelled probes are labelled with a radioactive isotope.

8. The method of claim 1 wherein said labelled probes are labelled with alkaline phosphatase.

9. The method of claim 1 wherein the amplification in step (a) is performed by polymerase chain reaction, ligase chain reaction, or self-sustained sequence replication.

10. The method of claim 9 wherein the amplification is performed by polymerase chain reaction.

11. The method of claim 1 wherein in step (e) the third labelled polynucleotide probe is contacted with the first and second portions of the amplified polynucleotide.

12. The method of claim 1 wherein in step (e) the third labelled polynucleotide probe is contacted with a third portion of the amplified polynucleotide.

* * * * *

SEQUENCE LISTING (1) GENERAL INFORMATION:

(iii) NUMBER OF SEQUENCES: 5

(2) INFORMATION FOR SEQ ID NO:1:

(i) SEQUENCE CHARACTERISTICS:
      (A) LENGTH: 27 base pairs
      (B) TYPE: nucleic acid
      (C) STRANDEDNESS: single
      (D) TOPOLOGY: linear (ii) MOLECULE TYPE: DNA (genomic)

(xi) SEQUENCE DESCRIPTION: SEQ ID NO:1:

AAATCCATAC AATACTCCAG TATTTGC      27

(2) INFORMATION FOR SEQ ID NO:2:

(i) SEQUENCE CHARACTERISTICS:
      (A) LENGTH: 28 base pairs
      (B) TYPE: nucleic acid

```
            (C) STRANDEDNESS: single
            (D) TOPOLOGY: linear (ii) MOLECULE TYPE: DNA (genomic)

(xi) SEQUENCE DESCRIPTION: SEQ ID NO:2:

ACCCATCCAA AGGAATGGAG GTTCTTTC                                              28

(2) INFORMATION FOR SEQ ID NO:3:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:3:

TGGGGRYTTA CCACRCCAGA                                                       20

(2) INFORMATION FOR SEQ ID NO:4:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:4:

TGGGGRYTTT WCACRCCAGA                                                       20

(2) INFORMATION FOR SEQ ID NO:5:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:5:

CAGGGATGGA AAGGATCACC                                                       20
```